(12) United States Patent
Han et al.

(10) Patent No.: US 10,799,202 B2
(45) Date of Patent: Oct. 13, 2020

(54) MAMMOGRAPHY SYSTEM

(71) Applicant: Vieworks Co., Ltd., Anyang-si, Gyeonggi-do (KR)

(72) Inventors: Dongkook Han, Siheung-si (KR); Soongil Hong, Cheonan-si (KR); Seokjong Kim, Namyangju-si (KR); Junghan Seo, Seoul (KR)

(73) Assignee: VIEWORKS CO., LTD., Anyang-si, Gyeonggi-do (KR)

( * ) Notice: Subject to any disclaimer, the term of this patent is extended or adjusted under 35 U.S.C. 154(b) by 14 days.

(21) Appl. No.: 16/269,039

(22) Filed: Feb. 6, 2019

(65) Prior Publication Data

US 2019/0239841 A1 Aug. 8, 2019

(30) Foreign Application Priority Data

Feb. 7, 2018 (KR) ........................ 10-2018-0015274

(51) Int. Cl.
*A61B 6/00* (2006.01)
*A61B 6/06* (2006.01)
*A61B 6/04* (2006.01)

(52) U.S. Cl.
CPC ................ *A61B 6/502* (2013.01); *A61B 6/06* (2013.01); *A61B 6/4291* (2013.01); *A61B 6/0414* (2013.01); *A61B 6/488* (2013.01)

(58) Field of Classification Search
None
See application file for complete search history.

(56) References Cited

U.S. PATENT DOCUMENTS

| 7,319,735 | B2 | 1/2008 | Defreitas et al. |
| 2011/0206181 | A1* | 8/2011 | Linev ............... A61B 6/502 378/37 |
| 2017/0245810 | A1* | 8/2017 | Maidment .......... A61B 6/461 |

FOREIGN PATENT DOCUMENTS

| EP | 0 417 964 A2 | 3/1991 |
| JP | 04-354940 A | 12/1992 |
| JP | 2010-110571 A | 5/2010 |
| JP | 2015-020028 A | 2/2015 |
| JP | 2017-012449 A | 1/2017 |
| KR | 10-2014-0118443 A | 10/2014 |
| KR | 10-1457099 B1 | 10/2014 |
| KR | 10-1620331 B1 | 5/2016 |
| KR | 10-2017-0039974 A | 4/2017 |

* cited by examiner

*Primary Examiner* — Hoon K Song
(74) *Attorney, Agent, or Firm* — Rabin & Berdo, P.C.

(57) ABSTRACT

The present invention relates to a mammography system including a body, an x-ray generator for irradiating x-rays, a collimator for adjusting an irradiation range of the x-rays, an arm frame rotatable in a clockwise or counterclockwise direction, and a rotating shaft for connecting the arm frame and the body, wherein the arm frame includes a compression stand having a compressor moving in up and down directions and a compression pad detachably coupled to the lower end of the compressor to compress the subject, and an imaging stand facing the x-ray generator and having a detector disposed at the inside thereof to detect the x-rays transmitted to the subject, the imaging stand moving in left and right directions with respect to the arm frame.

9 Claims, 14 Drawing Sheets

MAMMOGRAPHY SYSTEM

BACKGROUND OF THE INVENTION

Field of the Invention

The present invention relates to a mammography system for early diagnosis of breast cancer, and more particularly, to a mammography system that is configured to allow an imaging stand to move in left or right direction for a left or right mediolateral oblique (LMLO or RMLO) view of breast, thereby more improving conveniences in imaging manipulations and accuracy in imaging results when compared with conventional practices.

Background of the Related Art

A mammography system is medical equipment that is adapted to immobilize and compress a patient's breast as a subject, to irradiate x-rays to the subject, and to obtain an image of the inside of the subject by means of the x-rays transmitted to the subject, so that through the analysis of the image, breast cancer can be early diagnosed.

Standard imaging views for breast cancer diagnosis include a craniocaudal (CC) view in which the centers of left and right breasts are imaged from the top side to the bottom side and a mediolateral oblique (MLO) view in which left and right breasts are imaged in oblique directions.

So as to reduce an amount of x-rays irradiated in the imaging process for the CC and MLO views and to prevent a situation in which hidden lesions are not detected due to breast tissues laminated on each other from occurring, the breast as the subject has to be imaged in the state of being compressed. Since every man has different breast sizes, however, it is actually hard to effectively compress the breast of every man only with one size compression pad. So as to solve the problem, accordingly, compression pads of various sizes are prepared so that they are appropriately used according to the sizes of subjects to enhance the accuracy in breast cancer diagnosis. However, it is actually hard to prepare the compression pads adequate for all subject sizes, and accordingly, small breasts are often imaged in the state of being compressed by means of large compression pads.

In this case, it is difficult for a radiologist to adjust the position of the subject due to the relatively large compression pad, thereby making it hard to perform accurate imaging, and in conventional practices, accordingly, the compression pad compressing the subject moves in a left or right direction with respect to an arm frame, thereby trying to ensure conveniences in the radiologist's imaging manipulations.

Even in case where the compression pad moves horizontally, however, a force point for applying a compression force to the subject does not correspond to the center of the compression pad to which the compression force is applied, as shown in FIG. 1, so that the compression force applied to the subject cannot be reliable, and above all, stress is applied to the compression pad to cause the compression pad to be likely to be broken.

SUMMARY OF THE INVENTION

Accordingly, the present invention has been made in view of the above-mentioned problems occurring in the related art, and it is an object of the present invention to provide a mammography system that is configured, unlike the conventional mammography system, to allow not a compression pad, but an imaging stand to move in left and right directions, thereby improving conveniences in a radiologist's imaging manipulations, and to allow imaging for an MLO view to be carried out through the left and right movements of the imaging stand, without any vertical movement of an arm frame, even though a large x-ray detector is used, thereby optimizing advantages of an isocenter structure (wherein the imaging stand is located at a position corresponding to the isocenter of the arm frame).

The technical problems to be achieved through the present invention are not limited as mentioned above, and other technical problems not mentioned herein will be obviously understood by one of ordinary skill in the art through the following description.

To accomplish the above-mentioned object, according to the present invention, there is provided a mammography system including: a body; an x-ray generator for irradiating x-rays; a collimator for adjusting the irradiation range of the x-rays; an arm frame rotatable in a clockwise or counterclockwise direction in such a manner as to allow the x-ray generator to be located on an upper end thereof; and a rotating shaft for connecting the arm frame and the body, wherein the arm frame includes: a compression stand having a compressor moving in up and down directions according to a size of a subject and a compression pad detachably coupled to the lower end of the compressor to compress the subject; and an imaging stand facing the x-ray generator and having a detector disposed at the inside thereof to detect the x-rays transmitted to the subject, the imaging stand moving in left and right directions with respect to the arm frame in such a manner as to be located at a position corresponding to the isocenter of the arm frame.

According to the present invention, desirably, the imaging stand includes: a fixed support base coupled to one surface of the arm frame; and a moving support base located on top of the fixed support base in such a manner as to be movable in the left and right directions and having the detector disposed therein.

According to the present invention, desirably, the fixed support base includes a driving motor and a pinion gear coupled to a rotating shaft of the driving motor, and the moving support base includes a moving rail disposed on the underside corresponding to the pinion gear, so that as the pinion gear rotates, the moving support base moves in the left and right directions.

According to the present invention, desirably, the fixed support base includes at least one or more guide blocks each having a coupling groove formed thereon, and the moving support base includes guide members protruding from the underside thereof in such a manner as to be located at positions corresponding to the guide blocks, so that as the moving support base moves in the left and right directions, the guide members move along the coupling grooves of the guide blocks.

According to the present invention, desirably, the fixed support base includes a magnetic member disposed on top thereof, and the moving support base includes a fixing plate attached to the underside thereof, and otherwise, the fixed support base includes a fixing plate attached to top thereof, and the moving support base includes a magnetic member disposed on the underside thereof, so that the movement of the moving support base is braked by means of magnetic coupling between the magnetic member and the fixing plate.

According to the present invention, desirably, the magnetic member is an electromagnet or permanent electromagnetic holder.

According to the present invention, desirably, the moving support base moves in the left and right direction by a given distance at the same time when the arm frame rotates.

According to the present invention, desirably, if the arm frame rotates in a counterclockwise direction to perform imaging for an RMLO view, the moving support base moves in the left direction by a given distance, and if the arm frame rotates in a clockwise direction to perform imaging for an LMLO view, the moving support base moves in the right direction by a given distance.

According to the present invention, desirably, a moving distance of the moving support base in the left or right direction is varied according to the size of the compression pad or the rotating angle of the arm frame.

BRIEF DESCRIPTION OF THE DRAWINGS

The above and other objects, features and advantages of the present invention will be apparent from the following detailed description of one of the embodiments of the invention in conjunction with the accompanying drawings, in which.

DETAILED DESCRIPTION OF THE INVENTION

Figure 1:
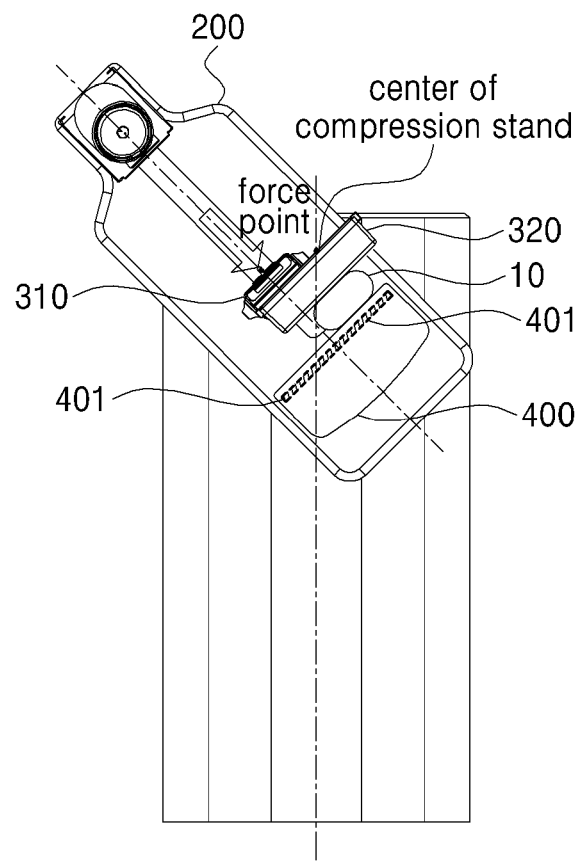
FIG. 1 is a front view showing an imaging process for an MLO view in a conventional mammography system wherein a compression pad moves in a horizontal direction.

Hereinafter, the present invention is disclosed with reference to the attached drawings wherein the corresponding parts in the embodiments of the present invention are indicated by corresponding reference numerals and the repeated explanation on the corresponding parts will be avoided. If it is determined that the detailed explanation on the well known technology related to the present invention makes the scope of the present invention not clear, the explanation will be avoided for the brevity of the description.

When it is said that one element is described as being "connected" or "coupled" to the other element, one element may be directly connected or coupled to the other element, but it should be understood that another element may be present between the two elements. In the description, when it is said that one member is located "above" another member, it means that one member may come into contact with another member as well as yet another member may exist between the two members.

In this application, terms, such as "comprise", "include", or 'have', are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

Before a mammography system according to the present invention is explained, first, the limitations in the conventional mammography system will be briefly described with reference to FIGS. 1 to 2B.

Figure 2A:
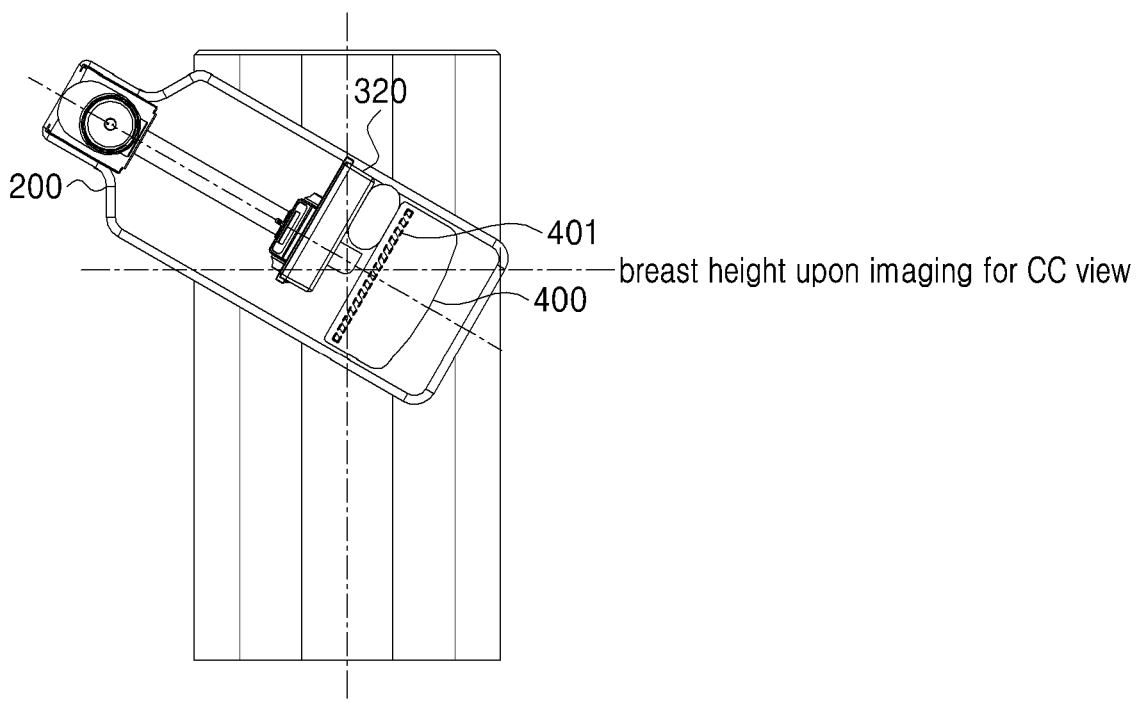
FIGS. 2A and 2B are front views showing problems occurring in the conventional mammography system when a large x-ray detector is used.
Figure 2B:
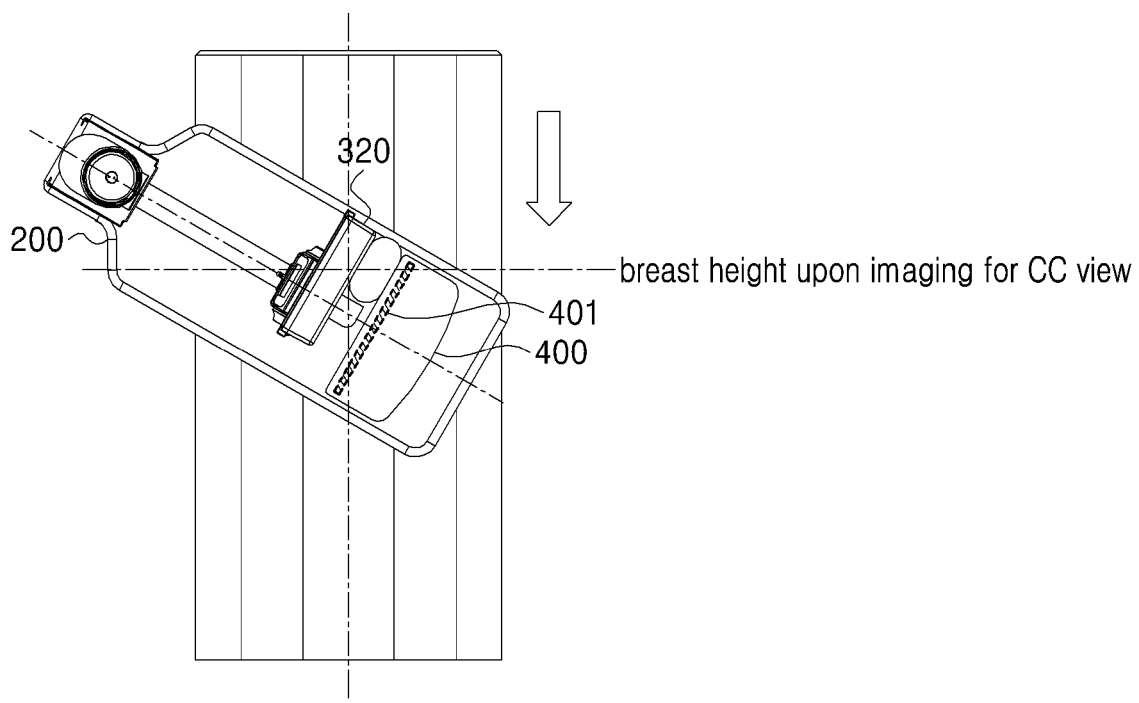

FIG. 1 is a front view showing an imaging process for an MLO view in a conventional mammography system wherein a compression pad moves in a horizontal direction, and FIGS. 2A and 2B are front views showing problems occurring in the conventional mammography system when a large x-ray detector is used.

At this time, the movement of a compression pad 320 in a horizontal direction means that the compression pad 320 moves to a left or right side in a parallel state to an imaging surface of an imaging stand 400, and the meaning will be used below with the same meaning.

At the time of breast cancer diagnosis through the mammography system, imaging is performed in a state where a subject 10 is compressed so as to enhance accuracy in the diagnosis, and in such case, the most important thing is to compress the subject 10 by means of the compression pad 320 adequate to the size of the subject 10.

Since every man has different breast sizes, however, it is actually hard to prepare compression pads having all sizes corresponding to the sizes of the subjects, and in the conventional mammography system, accordingly, the compression pad 320 moves in a horizontal direction, as shown in FIG. 1, so that even when the large compression pad 320 compresses the small subject 10, a radiologist's hand can come into close contact with the subject 10, thereby ensuring conveniences in his or her imaging manipulations.

Generally, the mammography system in real time measures a compression force applied to the subject 10 to obtain a mammography image corresponding to the compression force, but if the compression pad 320 moves in the horizontal direction, like the conventional mammography system, a force point for compressing the subject 10 does not correspond to the center of the compression pad 320, as shown in FIG. 1, so that stress occurs between a compressor 310 and the compression pad 320 to cause the compression pad 320 to be likely to be broken, and the compression force is not transmitted evenly to the subject 10 to make a compression force value measured by a sensor disposed on the compressor 310 not reliable, thereby making reliability of information on the mammography image deteriorated.

Upon imaging for an LMLO (left mediolateral oblique) or RMLO (right mediolateral oblique) view in the conventional practice, also, if a height of an imaging stand 400 is varied according to the rotation of an arm frame 200, it has to be adjusted to a patient's breast position, so that the arm frame 200 moves vertically, which makes the imaging time undesirably extended longer. So as to solve such problems, accordingly, there is provided a new structure (hereinafter, referred to as 'isocenter structure') wherein the imaging stand 400 is located at a position corresponding to the isocenter of the arm frame 200.

Even in case where the imaging stand 400 is located at a position corresponding to the isocenter of the arm frame 200, like this, if a large x-ray detector 401 is used, the arm frame 200 rotates in a clockwise or counterclockwise direction to perform imaging for the MLO view, and accordingly, a height of one side end of the imaging stand 400 becomes excessively raised, as shown in FIG. 2A.

Upon imaging for the RMLO view (which is the same as for the LMLO view) as shown in FIG. 2A, the patient's right armpit leans on the right side surface of the imaging stand 400, and accordingly, the subject 10 has to be located at the right end of the imaging stand 400, so that if the height of the right end of the imaging stand 400 is raised according to the rotation of the arm frame 200, it is impossible to perform the imaging, without any adjustment in position of the imaging stand 400, and accordingly, the arm frame 200 should move vertically, which undesirably extends imaging time.

Even though the compression pad 320 moves horizontally, the imaging stand 400 is not changed in position, and so as to perform the imaging for the MLO view, accordingly, the arm frame 200 has to move vertically, as shown in FIG. 2B.

In detail, the isocenter structure has a disadvantage that a relatively large torque is required to rotate the arm frame 200, but contrarily, it has an advantage that the height of the imaging stand 400 is adjustable to the minimum, so that it is applicable to the mammography system. If the large x-ray detector 401 is used, however, it is impossible to locate the subject 10 at the isocenter position upon imaging for the MLO view, thereby failing to obtain the advantage the isocenter structure has had. Even though the location of the compression pad 320 is adjusted like the conventional practice, moreover, the location of the imaging stand 400 is not changed, so that if the large x-ray detector 401 is used, accordingly, it is impossible to obtain the advantage the isocenter structure has had.

Unlike the conventional mammography system, accordingly, the mammography system according to the present invention is configured to allow not the compression pad 320, but the imaging stand 400 to move horizontally. That is, the force point and the center of the compression pad 320 correspond to each other to prevent the compression pad 320 from being broken, and it is possible to perform imaging for the MLO view, without any vertical movement of the arm frame 200, thereby solving the above-mentioned problems the conventional mammography system has had.

Hereinafter, an explanation on a mammography system according to the present invention will be given in detail with reference to FIGS. 3 to 7B.

Figure 3:
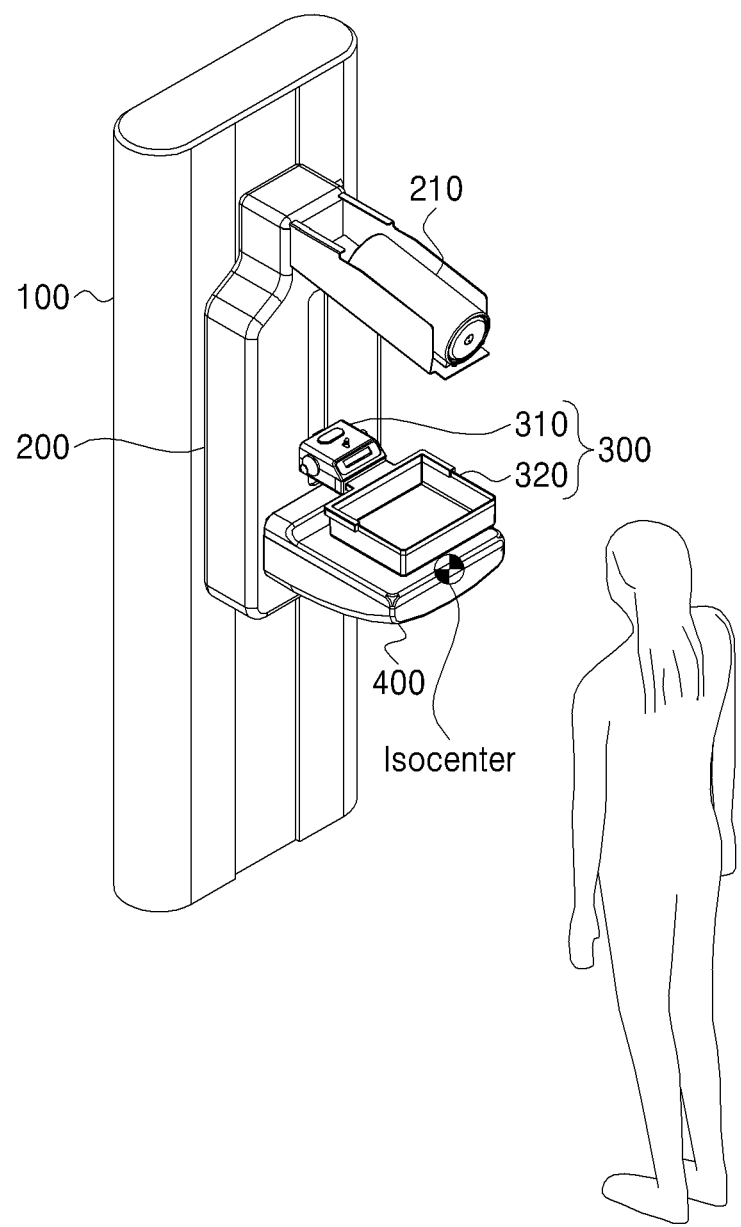
FIG. 3 is a perspective view showing a mammography system according to the present invention.
Figure 4:
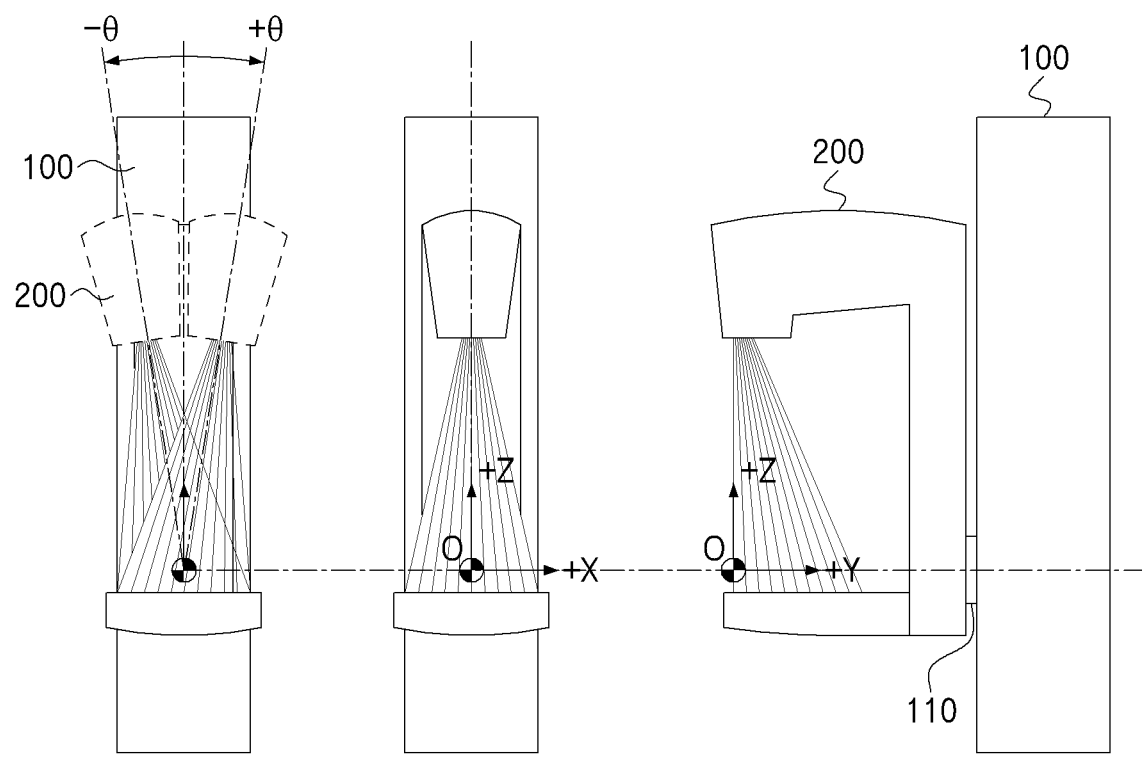
FIG. 4 shows the isocenter of an arm frame.
Figure 5A:
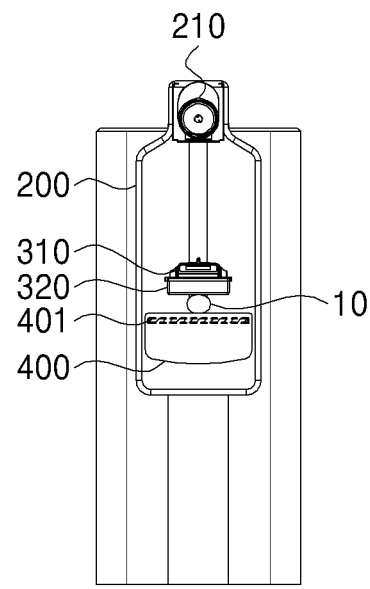
FIGS. 5A to 5C are front views showing the mammography system according to the present invention, to which different size compression pads are attached according to the sizes of subjects.
Figure 5B:
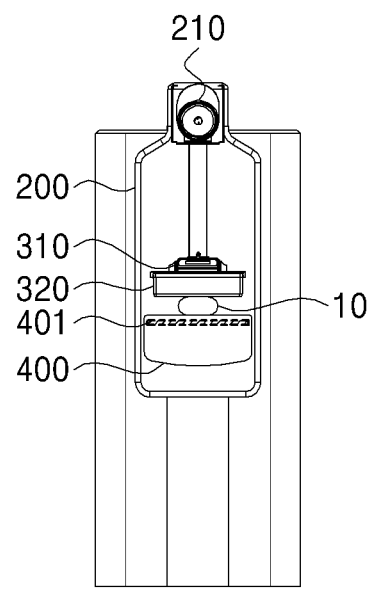
Figure 5C:
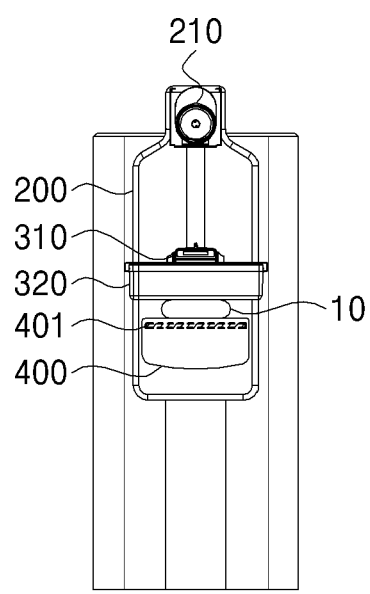
Figure 6:
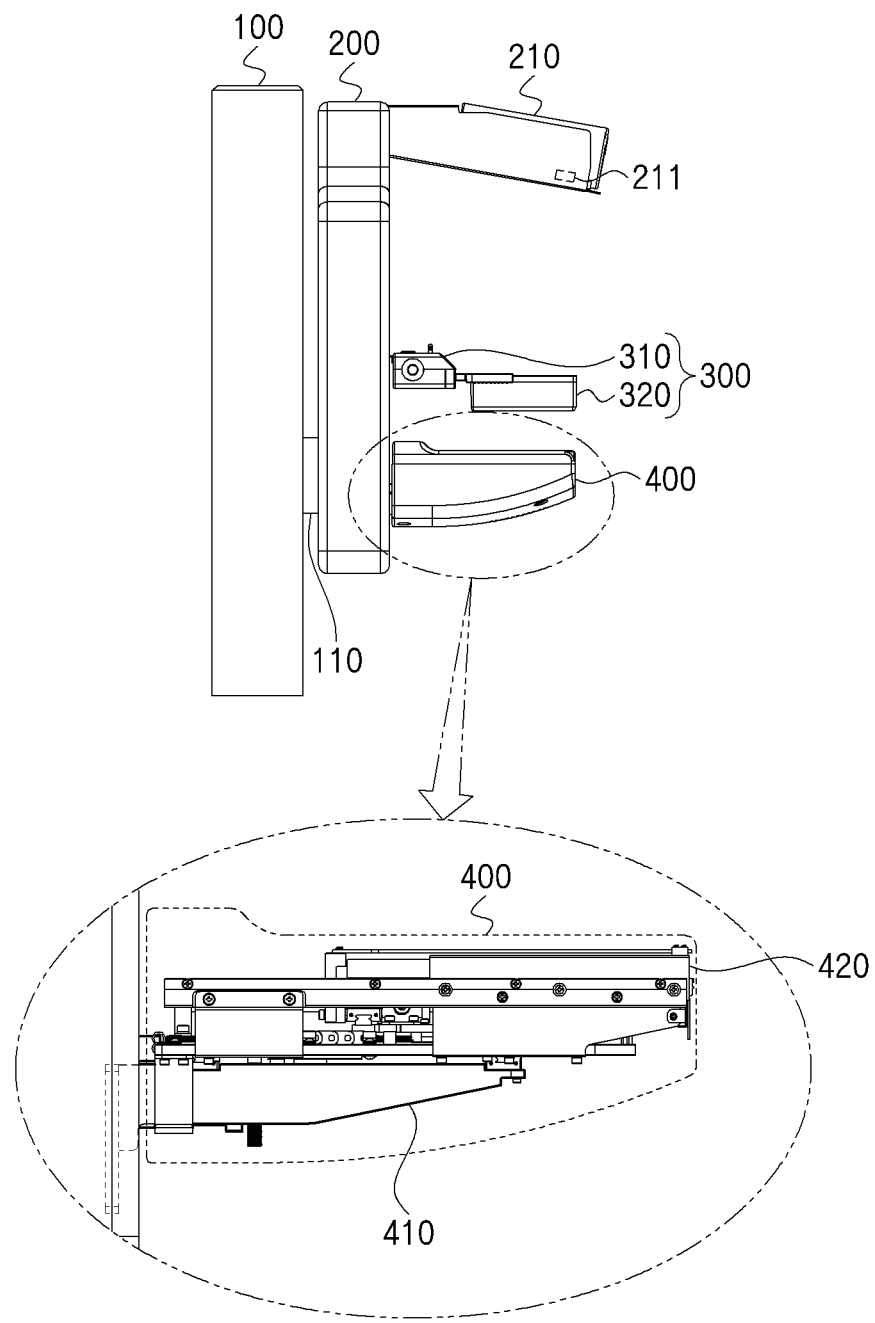
FIG. 6 is a side view showing the mammography system according to the present invention.
Figure 7A:
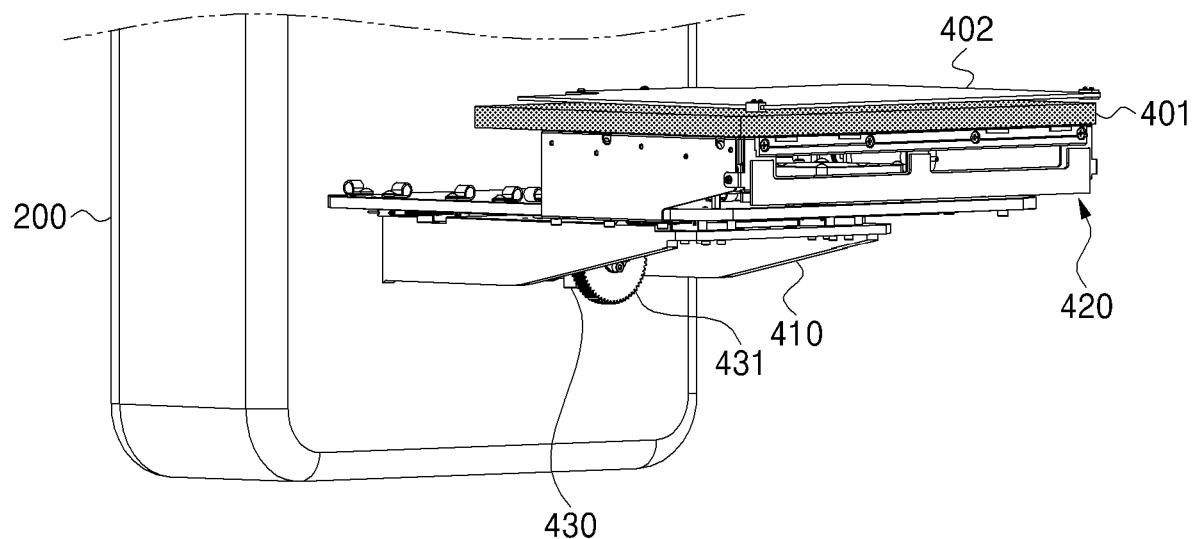
FIG. 7A is a perspective view showing an imaging stand of the mammography system according to the present invention.
Figure 7B:
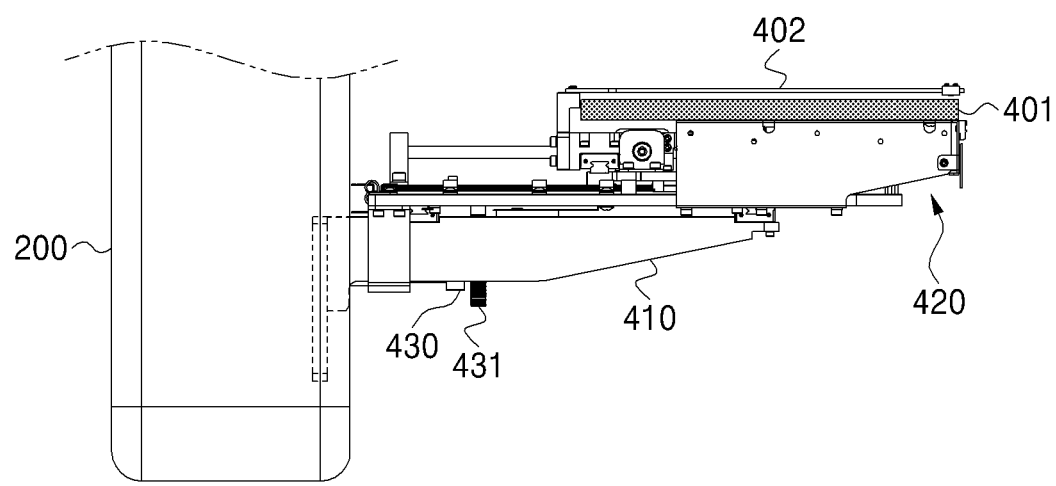
FIG. 7B is a side view showing the imaging stand of the mammography system according to the present invention.

FIG. 3 is a perspective view showing a mammography system according to the present invention, FIG. 4 shows the isocenter of an arm frame, FIGS. 5A to 5C are front views showing the mammography system according to the present invention, to which different size compression pads are attached according to the sizes of subjects, FIG. 6 is a side view showing the mammography system according to the present invention, FIG. 7A is a perspective view showing an imaging stand of the mammography system according to the present invention, and FIG. 7B is a side view showing the imaging stand of the mammography system according to the present invention.

According to the present invention, a mammography system includes: a column-shaped body 100; an x-ray generator 210 for irradiating x-rays; an arm frame 200 rotatable in a clockwise or counterclockwise direction with respect to the body 100 in such a manner as to locate the x-ray generator 210 on an upper end thereof; and a rotating shaft 110 for connecting the arm frame 200 and the body 100.

At this time, the arm frame 200 includes a compression stand 300 for compressing a subject 10 and an imaging stand 400 facing the x-ray generator 210 located on the upper end of the arm frame 200 and having a detector 401 disposed in the inside thereof to detect the x-rays transmitted to the subject 10. The imaging stand 400 is disposed on a position corresponding to the isocenter of the arm frame 200 rotating in the clockwise or counterclockwise direction within a given angle range, so that it can move horizontally in a left or right direction with respect to the arm frame 200.

In this case, the horizontal movement of the imaging stand 400 in the left or right direction with respect to the arm frame 200 means that the imaging stand 400 moves to the left or right side with respect to a vertical axis passing through the center of the arm frame 200, and the meaning will be used below with the same meaning.

Referring to the respective parts constituting the mammography system according to the present invention, first, the body 100 is a column-shaped frame and is coupled to the arm frame 200 by means of the rotating shaft 110, so that upon imaging for the LMLO view, the arm frame 200 rotates in the clockwise direction, and upon imaging for the RMLO view, the arm frame 200 rotates in the counterclockwise direction. Moreover, the arm frame 200 moves vertically to allow a patient's breast position to correspond to the height of the imaging stand 400 of the arm frame 200.

Next, the arm frame 200 is a '⊏'-shaped frame when viewed on the side, which is called 'C-arm' or 'gantry' because of its unique shape. The arm frame 200 includes the x-ray generator 210 for irradiating the x-rays to the subject 10, the compression stand 300 for compressing the subject 10 to make the subject 10 reduced in thickness, and the imaging stand 400 moving horizontally therearound in such a manner as to place the subject 10 on the top thereof.

Referring to the parts constituting the arm frame 200, first, the x-ray generator 210 is adapted to collide electrons having high kinetic energy against a metal to generate the x-rays to be irradiated to the subject 10.

Also, the x-ray generator 210 further includes a collimator 211 adapted to adjust the irradiation range of the x-rays generated therefrom and to avoid x-ray scattering.

The breast as the subject 10 is composed of only soft tissues, and unless a thickness of the breast is reduced through compression, a difference between x-ray attenuation coefficients in the tissues is not big, thereby obtaining no clear image. If the tissues are laminated on each other, hidden lesions may occur to make accuracy in breast cancer diagnosis undesirably deteriorated. Before the irradiation of x-rays to the subject 10, accordingly, the compression stand 300 serves to compress the subject 10 to make the subject 10 thinly flatten.

In detail, the compression stand 300 includes a compressor 310 moving in up and down directions along the direction of the vertical axis of the arm frame 200 according to the size of the subject 10 and a compression pad 320 coupled to the lower end of the compressor 310 to directly compress the subject 10. As the compressor 310 moves in the up and down directions, a force is transferred to the compression pad 320 coupled to the lower end of the compressor 310, and the compression pad 320 compresses the subject 10 to make the subject 10 thinly flatten with the force received from the compressor 310.

At this time, the compression pad 320 is detachably coupled to the compressor 310, and as shown in FIGS. 5A to 5C, the different size compression pads 320 are attached to the compressor 310 according to sizes of the subject 10, so that it is easy for a radiologist to adjust the position of the subject 10, thereby enhancing conveniences in his or her imaging manipulations. Further, the compressor 310 has a pressure sensor (not shown) disposed on the inside thereof to in real time measure a force compressing the subject 10.

Even if the compression pads 320 having different sizes are attached to the compressor 310 according to sizes of the subjects 10, it is actually hard to prepare the compression pads 320 having sizes corresponding to all of subjects, and according to the present invention, therefore, the imaging stand 400 on which the subject 10 is located moves upon imaging. Even if the small subject 10 is compressed against the large compression pad 320, as a result, many conveniences in the radiologist's imaging manipulations can be ensured.

As mentioned above, the imaging stand 400 is located at the position corresponding to the isocenter of the arm frame 200, and as shown in FIG. 4, the isocenter is a point not changed in position even when the arm frame 200 rotates in the clockwise or counterclockwise direction within the given angle range. As the imaging stand 400 is located at the isocenter not changed in position even in case of the rotation of the arm frame 200, a process of adjusting a vertical height of the arm frame 200 can be minimized upon imaging for the LMLO or RMLO view.

At the time of the breast cancer diagnosis through the mammography system, actually, most of time consumed for imaging is occupied by vertically moving the arm frame 200 to allow the imaging stand 400 to correspond to the patient's breast height, and according to the present invention, the imaging stand 400 is located at the isocenter of the arm frame 200, thereby minimizing the vertical movement of the arm frame 200 to allow imaging time to be shortened.

According to the present invention, moreover, the imaging stand 400 moves horizontally, while being located at the isocenter of the arm frame 200, thereby solving the problem occurring in the conventional mammography system that when the large x-ray detector is used, a height of one side end of the imaging stand 400 is raised to make the arm frame 200 move vertically.

The imaging stand 400 includes a fixed support base 410 and a moving support base 420 so that it can move horizontally in the left and right directions with respect to the arm frame 200. Hereinafter, an explanation on the fixed support base 410 and the moving support base 420 will be in detail given with reference to FIGS. 7A to 10.

Figure 8:
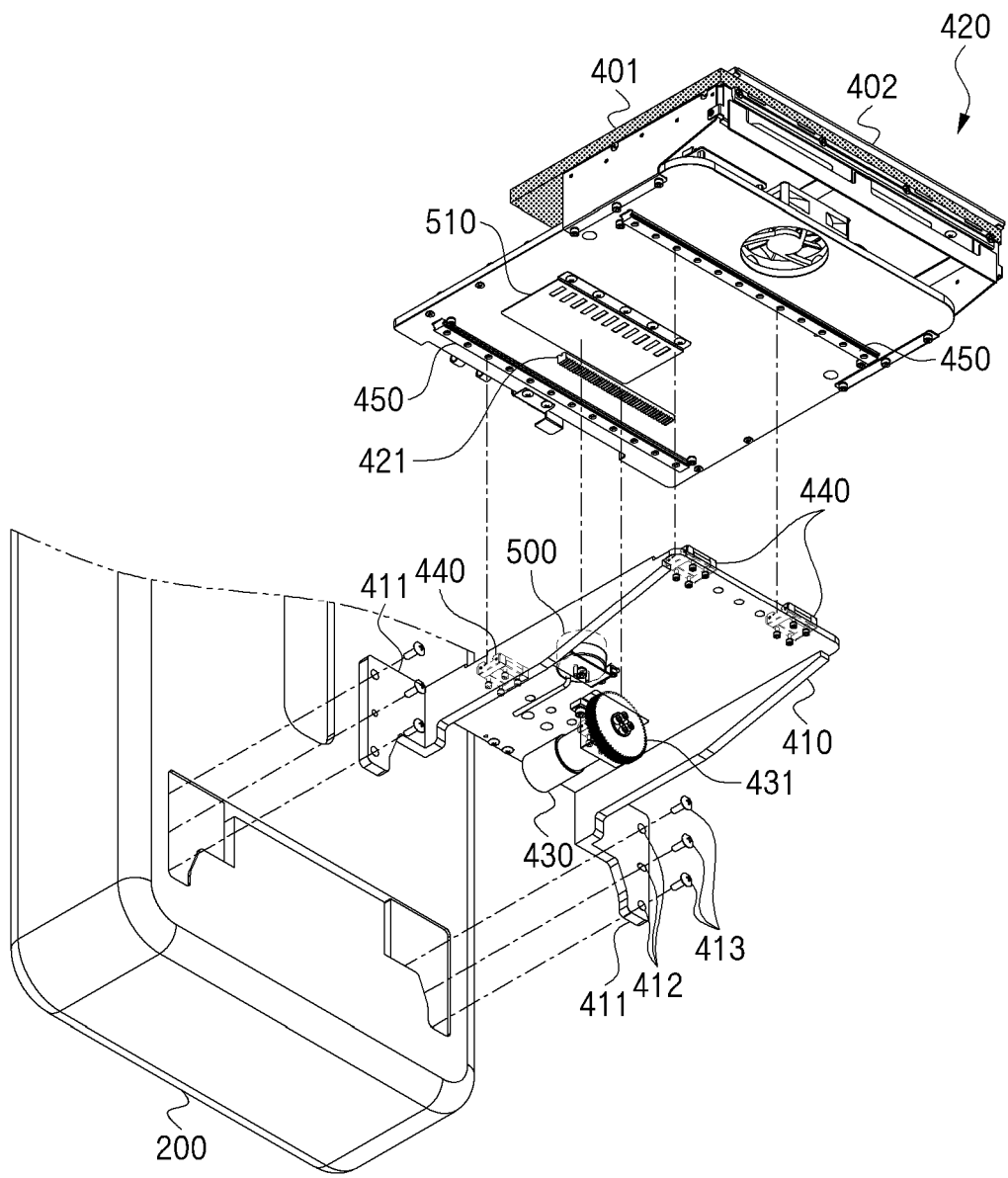
FIG. 8 is an exploded perspective view showing a fixed support base and a moving support base of the imaging stand of the mammography system according to the present invention.
Figure 9:
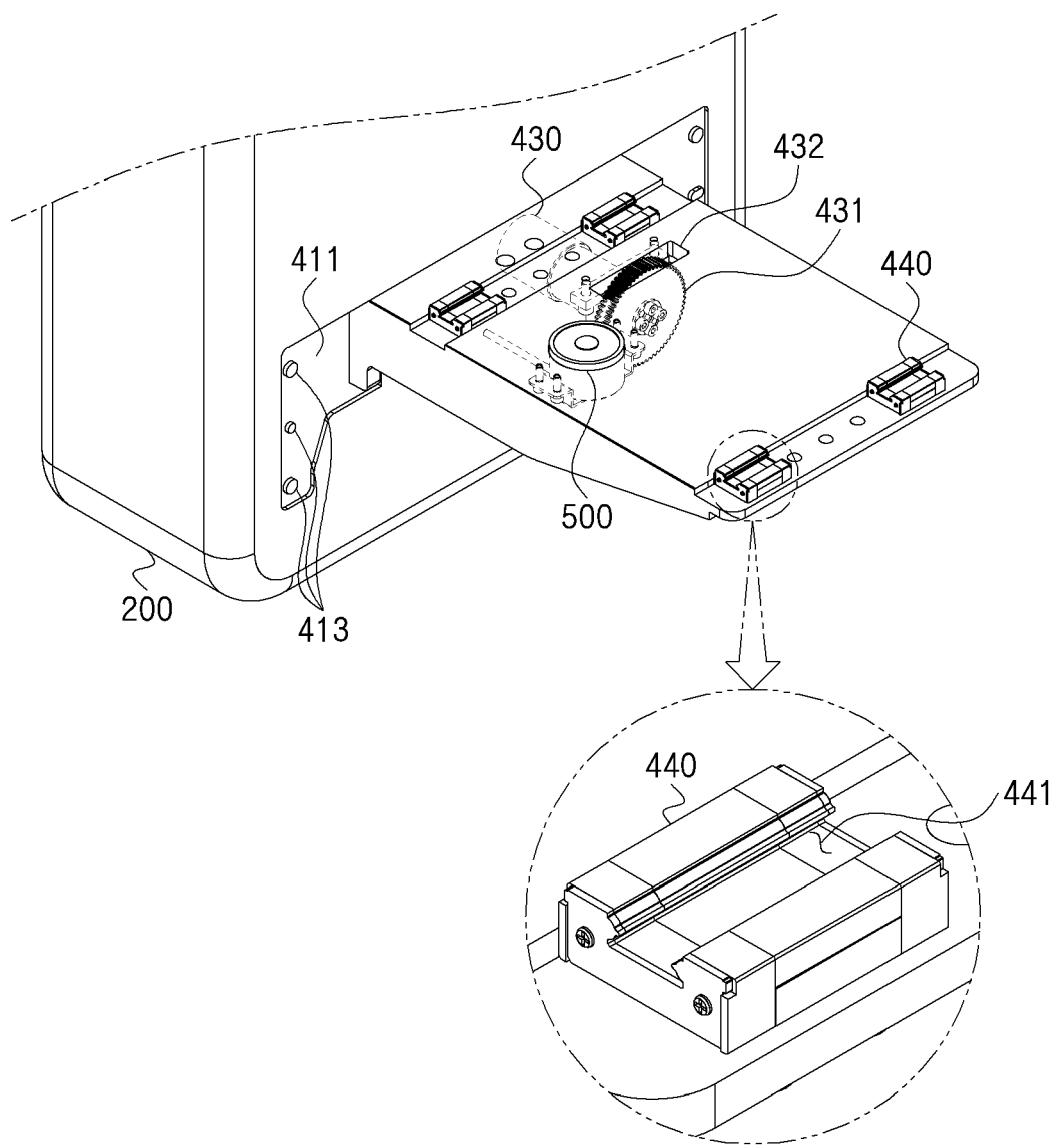
FIG. 9 is an enlarged view showing the fixed support base of the imaging stand of the mammography system according to the present invention.
Figure 10:
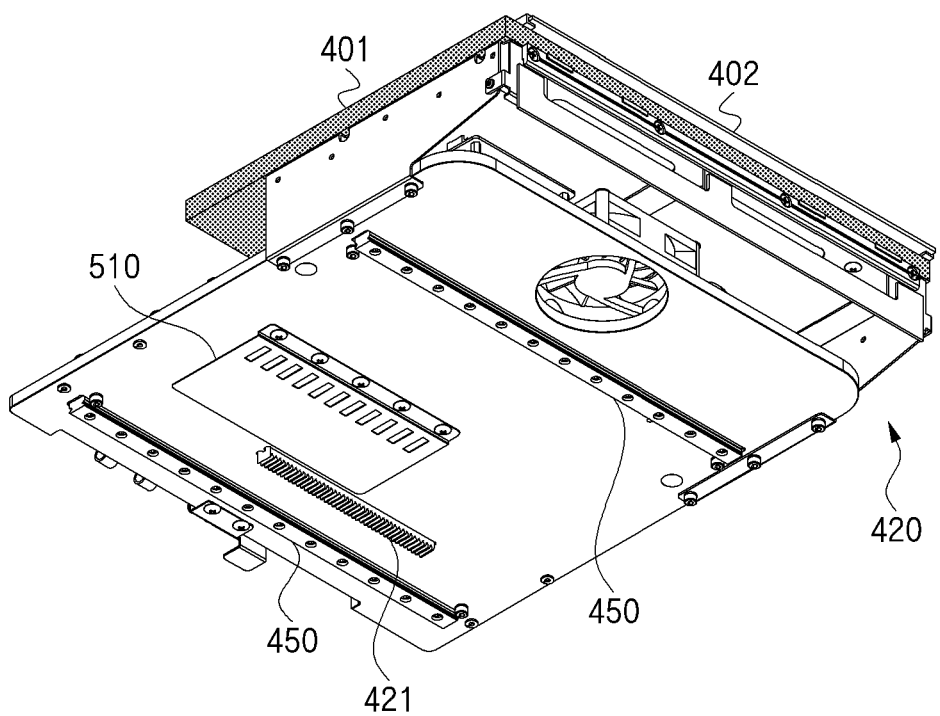
FIG. 10 is an enlarged view showing the moving support base of the imaging stand of the mammography system according to the present invention.

FIG. 7A is a perspective view showing the imaging stand of the mammography system according to the present invention, FIG. 7B is a side view showing the imaging stand of the mammography system according to the present invention, FIG. 8 is an exploded perspective view showing the fixed support base and the moving support base of the imaging stand of the mammography system according to the present invention, FIG. 9 is an enlarged view showing the fixed support base of the imaging stand of the mammography system according to the present invention, and FIG. 10 is an enlarged view showing the moving support base of the imaging stand of the mammography system according to the present invention.

The imaging stand 400 includes the fixed support base 410 fixedly coupled to one surface of the arm frame 200 and the moving support base 420 located on top of the fixed support base 410 in such a manner as to be movable in the left and right directions.

As shown in FIG. 8, the fixed support base 410 includes a fixing member 411 disposed on one surface coming into contact with the arm frame 200 and having a plurality of screw coupling holes 412 formed on left and right sides thereof in such a manner as to insert screws 413 thereinto, so that the fixed support base 410 is screw-coupled to the arm frame 200 by means of the screws 413 inserted into the screw coupling holes 412.

As the fixed support base 410 is fixedly coupled to the arm frame 200, the imaging stand 400 can resist load of the subject 10, and also, the fixed support base 410 is located on the underside of the moving support base 420, so that even if the subject 10 is changed in position during the imaging to make a direction to which the load is applied varied, the fixed support base 410 serves to maintain the whole balance of the imaging stand 400 to prevent the imaging stand 400 from swinging to the left and right sides.

The moving support base 420 is located on top of the fixed support base 410 fixedly coupled to the arm frame 200 and has an x-ray detector 401 disposed on the inside thereof to detect the x-rays transmitted to the subject 10.

The detector 401 generates an electrical signal by position according to amounts of incident x-rays transmitted to the subject 10 and produces a tomography image of the subject 10 on the basis of the generated electrical signal and position information. At this time, a grid 402 is disposed on top of the detector 401 to prevent the scattered x-rays from penetrating, so that the accuracy in the x-ray image can be improved.

Moreover, the moving support base 420 moves in left and right directions with respect to the fixed support base 410 so as to ensure conveniences in the imaging manipulations.

So as to move horizontally, in detail, the moving support base 420 includes a moving rail 421, which serves as a rack gear, disposed on the underside thereof, as shown in FIG. 10, and the fixed support base 410 includes a driving motor 430 attached to the underside thereof and a pinion gear 431 coupled to a rotating shaft of the driving motor 430.

At this time, the pinion gear 431 is coupled to the moving rail 412 disposed at the position corresponding thereto through a slot 432 formed in a straight line on the fixed support base 410, so that as the driving motor 430 rotates, the moving support base 420 can move horizontally to the left and right directions.

In addition to the horizontal movement of the moving support base 420 by means of the rack and pinion structure as mentioned above, of course, the horizontal movement of the moving support base 420 may be carried out by means of connection to the fixed support base 410 through a linear motion guide, by means of connection to the fixed support base 410 through a ball screw actuator, and by means of a linear motor disposed on the fixed support base 410.

Further, the imaging stand 400 includes guide blocks 440 each having a coupling groove 441 formed thereon and guide members 450 coupled to the coupling grooves 441 of the guide blocks 440. In detail, as shown in FIGS. 9 and 10, the guide blocks 440 are disposed on top of the fixed support base 410 fixed to the arm frame 200, and the guide members 450 protrude to the shapes corresponding to the coupling grooves 441 from the underside of the moving support base 420 moving horizontally (toward the fixed support base 410), so that even though the moving support base 420 moves horizontally, the guide blocks 440 for supporting the compression force applied from the compression pad 320 are not changed in position, thereby allowing the compression force to be transmitted evenly to the moving support base 420 and the subject 10 located between the moving support base 420 and the compression pad 320.

Contrarily, if the guide blocks 440 are disposed on the underside of the moving support base 420 moving horizontally and the guide members 450 protruding from top of the fixed support base 410 toward the moving support base 420, the guide blocks 440 may escape in position from a center line to which the compression force is applied, so that the parallel relationship between the compression pad 320 and the imaging stand 400 is broken to make the compression force not transmitted evenly to the subject 10.

At this time, as shown in FIG. 9, each coupling groove 441 has a shape of '⊏', but may have a shape of 'U', without being limited thereto. Further, the guide blocks 440 may be disposed only on the front or rear end of the fixed support base 410, but as shown in FIG. 9, the guide blocks 440 are desirably disposed on the left and right sides of the front end of the fixed support base 410 and on the left and right sides of the rear end thereof, thereby enhancing stability in the horizontal movement of the moving support base 420.

Furthermore, the fixed support base 410 includes a magnetic member 500 disposed on top thereof, and the moving support base 420 includes a fixing plate 510 disposed at a position corresponding to the magnetic member 500 to control the horizontal movement of the moving support base 420.

In detail, the fixing plate 510 is made of a magnetic material and is thus coupled magnetically to the magnetic member 500. According to the present invention, the horizontal movement of the moving support base 420 is braked by means of the magnetic coupling between the magnetic member 500 and the fixing plate 510.

Particularly, the magnetic member 500 is an electromagnet or permanent electromagnetic holder, and accordingly, a magnetic force of the magnetic member 500 is adjusted by means of current to allow the movement of the moving support base 420 to be braked. For example, if the magnetic member 500 is an electromagnet, current flows to the magnetic member 500 to make the magnetic member 500 have a magnetic force, thereby braking the movement of the moving support base 420, and contrarily, if the magnetic member 500 is a permanent electromagnetic holder, normally, current flows to the magnetic member 500 to make the magnetic member 500 not have a magnetic force. If it is desired to brake the movement of the moving support base 420, the current is cut off to make the permanent electromagnetic holder have the magnetic force, thereby braking the movement of the moving support base 420.

According to the present invention, the magnetic coupling between the magnetic member 500 and the fixing plate 510 enables the movement of the moving support base 420 to a given distance to be controlled upon imaging for the LMLO or RMLO view.

In case where power is cut off due to power failure during the imaging for the MLO view, further, if the magnetic member 500 is an electromagnet, reserve power is utilized to make the magnetic member 500 have a magnetic force, thereby preventing the moving support base 420 from sliding downward by means of gravity, and contrarily, if the magnetic member 500 is a permanent electromagnetic holder, power is cut off to make the magnetic member 500 have a magnetic force, thereby preventing the moving support base 420 from sliding downward by means of gravity.

A structure wherein the magnetic member 500 is disposed on top of the fixed support base 410 and the fixing plate 510 is disposed at a position of underside of the moving support base 420 corresponding to the magnetic member 500 has been suggested, but of course, a structure wherein the magnetic member 500 is disposed on underside of the moving support base 420 and the fixing plate 510 is disposed on top of the fixed support base 410 may be suggested, without being limited thereto.

Figure 11A:
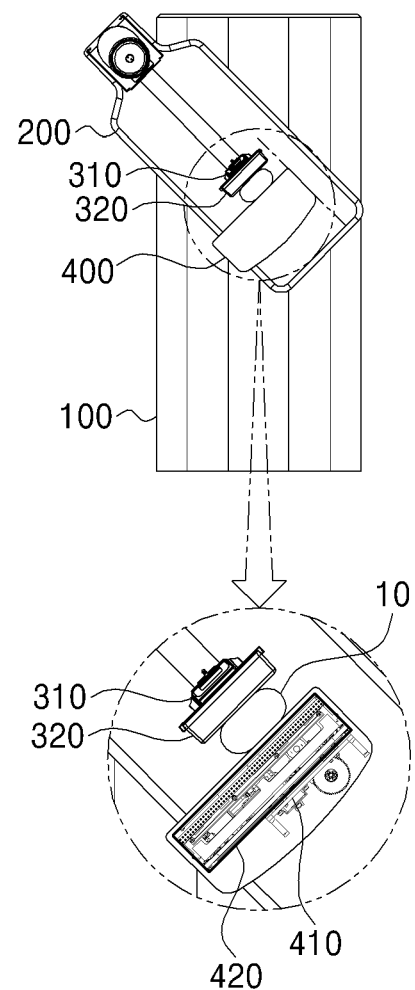
FIGS. 11A to 11C are front views showing driving states of the mammography system according to the present invention for CC and MLO views.
Figure 11B:
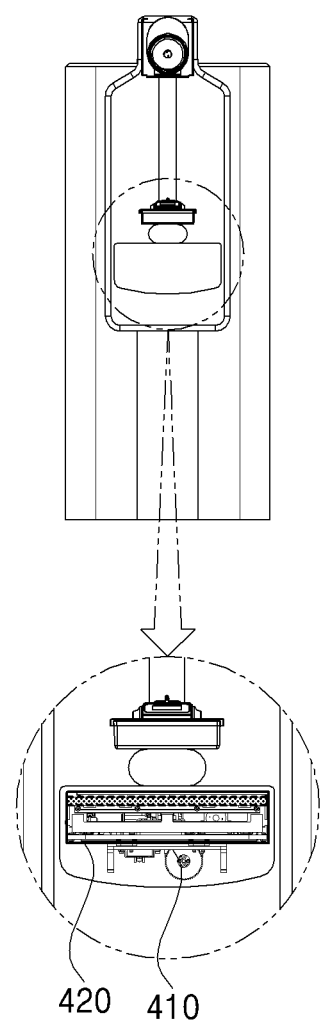
Figure 11C:
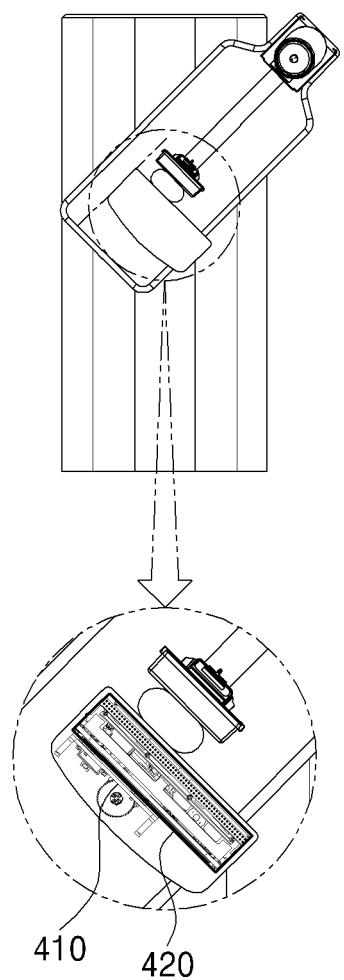

Next, an explanation on a process of controlling a position of the imaging stand 400 upon imaging for the CC and MLO views through the mammography system according to the present invention will be in detail given with reference to FIGS. 11A to 11C.

As shown in FIGS. 11A to 11C, the arm frame 200 does not need to rotate upon imaging for the CC view. However, the arm frame 200 has to rotate in a clockwise direction by a given angle upon imaging for the LMLO view, and it has to rotate in a counterclockwise direction by a given angle upon imaging for the RMLO view.

In the conventional mammography system, as briefly described above, one side end of the imaging stand 400 is excessively raised, as shown in FIG. 2A, upon imaging for the MLO view, and unless the height of the imaging stand 400 is adjusted, accordingly, the patient's breast does not come into contact with the imaging stand 400, so that the height of the arm frame 200 has to be adjusted to allow the right end of the imaging stand 400 to be located on the horizontal line of the isocenter, which undesirably extending the imaging time.

So as to perform the imaging for the MLO view in the mammography system according to the present invention, contrarily, the arm frame 200 rotates in the clockwise or counterclockwise direction, and at the same time, the imaging stand 400, especially, the moving support base 420 moves horizontally in the left and right directions by the given distance, so that even if the arm frame 200 rotates, one side end of the imaging stand 400 cannot be raised. Even upon imaging for the MLO view, accordingly, the subject 10 can be located at the isocenter, without any separate adjustment in the height of the arm frame 200, thereby more shortening the imaging time when compared with the conventional mammography system.

In detail, if the arm frame 200 rotates in the counterclockwise direction by a given angle θ so as to perform imaging for the RMLO view of the right breast, the moving support base 420 moves in the left direction by a given distance at the same time, and if the arm frame 200 rotates in the clockwise direction by the given angle θ so as to perform imaging for the LMLO view of the left breast, the moving support base 420 moves in the right direction by a given distance at the same time. Even if the arm frame 200 rotates, as a result, the subject 10 can be located at the isocenter.

At this time, the clockwise and counterclockwise directions are determined on the basis of directions when the patient who stands in front of the mammography system sees the mammography system.

A moving distance of the moving support base 420 in the left or right direction by the given distance is varied according to the size of the compression pad 320 or the rotating angle of the arm frame 200. According to the present invention, small, medium, and large compression pads 320 are prepared according to the sizes of the subject 10, and the compressor 310 has a size measuring sensor (not shown) adapted to sense the size of the compression pad 320. If the small compression pad 320 is attached, the moving support base 420 is set to move in the left or right direction by 15 cm, if the medium compression pad 320 is attached, the moving support base 420 is set to move in the left or right direction by 10 cm, and if the large compression pad 320 is attached, the moving support base 420 is set to move in the left or right direction by 5 cm. However, such setting of the moving distance of the moving support base 420 according to the sizes of the compression pad 320 is just one example, and therefore, it has to be understood that the moving distance may be varied according to use environments of the mammography system.

So as to allow the subject 10 to be located at the isocenter, at this time, the moving distance is desirably set to allow the right end of the compression pad 320 and the right end of the imaging stand 400 to be located on the same line as each other, upon imaging for the RMLO view, and to allow the left end of the compression pad 320 and the left end of the imaging stand 400 to be located on the same line as each other, upon imaging for the LMLO view. So as to allow the subject 10 to be located at the isocenter, more desirably, the moving distance is set to allow the right end of the compression pad 320 and the right end of the detector 401 of the imaging stand 400 to be located on the same line as each other, upon imaging for the RMLO view, and to allow the left end of the compression pad 320 and the left end of the detector 401 of the imaging stand 400 to be located on the same line as each other, upon imaging for the LMLO view.

The greater a rotation angle of the arm frame 200 is, the longer a moving distance of the moving support base 420 is, so that a height of the imaging stand 400 is maintained to correspond to the patient's breast height.

In conclusion, the mammography system according to the present invention is configured to allow the imaging stand itself to move horizontally, so that the radiologist's hand comes into contact with the subject, thereby improving conveniences in his or her imaging manipulations, and the imaging stand moves horizontally upon imaging for the MLO view, thereby needing no adjustment in the vertical height of the arm frame to more reduce the imaging time when compared with the conventional mammography system.

As described above, the mammography system according to the present invention is configured to allow the imaging stand to move horizontally even if the different size compression pads according to the sizes of the subjects are not prepared, so that the radiologist's hand is easily brought into contact with the subject, thereby improving conveniences in his or her imaging manipulations.

Unlike the conventional mammography system, further, the compression pad of the present invention does not move to allow a state where the force point for applying a compression force to the subject corresponds to the center of the compression pad to be maintained to evenly apply the compression force to the whole surface of the subject, thereby improving the accuracy in the imaging for the CC and MLO views.

In addition, the mammography system according to the present invention is configured, even though the large x-ray detector is used, to allow the subject to be located at the isocenter through the horizontal movement of the imaging stand, so that it is possible to perform imaging for the MLO view, without any adjustment in a height of the arm frame, thereby greatly reducing the imaging time and also optimizing advantages of the isocenter structure.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

Further, terms used in this application are used to only describe specific exemplary embodiments and are not intended to restrict the present invention. An expression referencing a singular value additionally refers to a corresponding expression of the plural number, unless explicitly limited otherwise by the context.

It is therefore intended that the scope of the invention be limited not by this detailed description, but rather by the claims appended hereto, and also, it is to be understood that all technical ideas in the same range as above are within the scope of the invention.

What is claimed is:

1. A mammography system comprising:
a body;
an x-ray generator for irradiating x-rays;
a collimator for adjusting an irradiation range of the x-rays;
an arm frame rotatable in a clockwise or counterclockwise direction in such a manner as to allow the x-ray generator to be located on an upper end thereof; and
a rotating shaft for connecting the arm frame and the body,
wherein the arm frame comprises:
a compression stand having a compressor moving in up and down directions according to a size of a subject and a compression pad detachably coupled to a lower end of the compressor to compress the subject; and
an imaging stand facing the x-ray generator and having a detector disposed at an inside thereof to detect the x-rays transmitted to the subject,
wherein the imaging stand comprises:
a fixed support base coupled to one surface of the arm frame; and
a moving support base located on top of the fixed support base in such a manner as to be movable in left and right directions and having the detector disposed therein;
wherein the fixed support base comprises a driving motor and a pinion gear coupled to a rotating shaft of the driving motor, and the moving support base comprises a moving rail disposed on an underside corresponding to the pinion gear, so that as the pinion gear rotates, the moving support base moves in the left and right directions.

2. The mammography system according to claim 1, wherein the image stand is located at a position corresponding to an isocenter of the arm frame.

3. The mammography system according to claim 1, wherein the fixed support base comprises at least one or more guide blocks each having a coupling groove formed thereon, and the moving support base comprises guide members protruding from the underside thereof in such a manner as to be located at positions corresponding to the guide blocks, so that as the moving support base moves in the left and right directions, the guide members move along the coupling grooves of the guide blocks.

4. The mammography system according to claim 1, wherein the fixed support base comprises a magnetic member disposed on top thereof, and the moving support base comprises a fixing plate attached to the underside thereof, so that movement of the moving support base is braked by means of magnetic coupling between the magnetic member and the fixing plate.

5. The mammography system according to claim 1, wherein the fixed support base comprises a fixing plate attached to the top thereof, and the moving support base comprises a magnetic member disposed on the underside thereof, so that movement of the moving support base is braked by means of magnetic coupling between the magnetic member and the fixing plate.

6. The mammography system according to claim 4, wherein the magnetic member is an electromagnet or permanent electromagnetic holder.

7. The mammography system according to claim 5, wherein the magnetic member is an electromagnet or permanent electromagnetic holder.

8. A mammography system comprising:
a body;
an x-ray generator for irradiating x-rays;
a collimator for adjusting an irradiation range of the x-rays;
an arm frame rotatable in a clockwise or counterclockwise direction in such a manner as to allow the x-ray generator to be located on an upper end thereof; and
a rotating shaft for connecting the arm frame and the body,
wherein the arm frame comprises:
a compression stand having a compressor moving in up and down directions according to a size of a subject and a compression pad detachably coupled to the lower end of the compressor to compress the subject; and
an imaging stand facing the x-ray generator and having a detector disposed at the inside thereof to detect the x-rays transmitted to the subject;
wherein the imaging stand comprises:
a fixed support base coupled to one surface of the arm frame; and
a moving support base located on top of the fixed support base in such a manner as to be movable in left and right directions and having the detector disposed therein,
wherein the moving support base moves in a left or right direction by a given distance at a same time as when the arm frame rotates;
wherein if the arm frame rotates in a counterclockwise direction to perform imaging for a right mediolateral oblique (RMLO) view, the moving support base moves in the left direction by a given distance, and if the arm frame rotates in a clockwise direction to perform imaging for a left mediolateral oblique (LMLO) view, the moving support base moves in the right direction by a given distance.

9. The mammography system according to claim 8, wherein a moving distance of the moving support base in the left or right direction is varied according to a size of the compression pad or a rotating angle of the arm frame.

* * * * *